United States Patent [19]

Bräutigam

[11] 4,263,260

[45] Apr. 21, 1981

[54] HIGH PRESSURE AND HIGH TEMPERATURE HEAT EXCHANGER

[75] Inventor: Max Bräutigam, Ottobrunn, Fed. Rep. of Germany

[73] Assignee: Linde Aktiengesellschaft, Wiesbaden, Fed. Rep. of Germany

[21] Appl. No.: 55,603

[22] Filed: Jul. 9, 1979

[30] Foreign Application Priority Data

Jul. 10, 1978 [DE] Fed. Rep. of Germany ....... 2830225
Jan. 30, 1979 [DE] Fed. Rep. of Germany ....... 2903466

[51] Int. Cl.³ ............................................. F28D 7/02
[52] U.S. Cl. .................................... 422/201; 165/156; 165/163; 422/205
[58] Field of Search ................ 422/173, 198, 200–203, 422/205; 165/156, 158, 160, 163

[56] References Cited

U.S. PATENT DOCUMENTS

| | | | |
|---|---|---|---|
| 2,500,519 | 3/1950 | Clark | 422/198 X |
| 3,126,949 | 3/1964 | Boni, Jr. et al. | 165/160 X |
| 3,524,725 | 8/1970 | Cremer et al. | 422/202 X |
| 3,696,636 | 10/1972 | Mille | 165/160 X |
| 4,163,470 | 8/1979 | Johnsen et al. | 165/160 X |

Primary Examiner—William A. Cuchlinski, Jr.
Attorney, Agent, or Firm—Karl F. Ross

[57] ABSTRACT

A heat exchanger, reactor or like apparatus capable of carrying out heat exchange, material exchange or combinations thereof, comprises a cylindrical housing formed at one end with a cover and provided internally with a cylindrical partition carried by the cover and reaching toward but terminating short of the opposite end of the housing to subdivide the interior into an inner chamber or space and an outer annular chamber or space. A first fluid is fed to a helical-coil tube bundle in the outer space and then passes into a helical-coil tube bundle in the inner space before being discharged through a manifold and pipe in the cover disposed centrally. The inlet pipe or pipes are also carried by the cover outwardly of the central pipe. The conduits for the second fluid which open into the spaces and which pass around the heat exchanger pipes in these spaces are also carried by the cover and may extend coaxially with the first fluid conduits.

28 Claims, 11 Drawing Figures

HIGH PRESSURE AND HIGH TEMPERATURE HEAT EXCHANGER

FIELD OF THE INVENTION

The present invention relates to a vessel adapted to be used as a heat exchanger and/or reactor and, more particularly, to a high-temperature and high-pressure heat exchanger, especially adapted to be used in the synthesis of methane. The invention also relates to a method of making such a heat exchanger or reactor.

BACKGROUND OF THE INVENTION

While there are a large number of heat exchangers or chemical reactors capable of effecting indirect heat exchange between two fluids, e.g. in the simple heating and cooling of a first fluid by a second fluid or in the thermal induction of a reaction in a first fluid by heat supplied by a second fluid or for the abstraction of reaction heat of the first fluid by a second fluid, problems continue to be encountered, especially when the reactor must be operated at high temperatures and with elevated pressures.

In such cases, significant technological problems arise. for example, when the operating temperature must be 900° to 1300° K., or in a similar range, the components of the heat exchanger must be composed, at least at the so-called hot end, of special alloys which are expensive and frequently have limited strength. When in addition, the fluids are under pressure, the problem is accentuated since the wall thickness of any stressed parts must be increased, thereby raising the cost of the unit.

The heat exchanger must have large dimensions to be practical for a particular chemical or other process, the reactor or heat exchanger cannot be designed from standard tables because of the higher wall thickness, special materials, etc. In fact, some of the refractory alloys which may be required are not conveniently available in large quantities. The weight of the reactor can become prohibitive in that the unit can no longer be readily transported by standard commercial means.

This applies to heat exchangers having a cylindrical housing and a tube bundle therein to which one of the fluids is admitted at one end and removed at the other, to heat exchangers in which a fluid is admitted to the housing around a tube bundle at one end and systems in which access to the space within the housing is effected through the cylindrical wall of the casing or shell.

In a coiled-tube exchanger, moreover, while it is common practice to wind the coils of the tube bundle on a core tube or pipe by rotating the later between end supports, the size of the heat exchanger which can be fabricated is limited by the weight of the tubes which can be supported by the tubular core. In practice, the coil continues to a point just before buckling of the core tube and this buckling point limits the size of the heat exchanger bundle which can be formed on the tube.

Naturally, it is possible to increase the mass of pipe which can be carried by using a core tube of larger diameter, but this requires a trade-off since it increases the useless volume, i.e. the space occupied by the core tube.

OBJECTS OF THE INVENTION

It is the principal object of the present invention to provide an improved heat exchanger for the purposes described which is capable of operating at high pressures and high temperatures, which can be fabricated at low cost and which, in general, overcomes the disadvantages of the earlier systems mentioned above.

Another object of this invention is to provide an improved method of making a heat exchanger or reactor which will allow the product to be larger in size than has hitherto been practical, consistent with the transport and other limits mentioned above.

SUMMARY OF THE INVENTION

These objects and others which will become apparent hereinafter are attained, in accordance with the present invention, by providing the heat exchanger as a preferably upright structure with a cylindrical housing formed at its upper end with a cover and its lower end with a closed bottom.

According to the invention, a cylindrical partition or sleeve extends axially within this vessel from the cover to a location close to but spaced from the bottom to subdivide the interior into an annular outer space and an inner space along the axis of the vessel.

According to the invention, respective tube bundles, preferably of helically coiled heat exchanger tubes (although straight tubes can be used alone or interspersed or combined with helical tubes) are provided in each of the spaces, i.e. between the partition and the shell of the heat exchanger on the one hand and within the partition on the other hand.

According to the invention, the means forming the tube bundles include tubes for a first fluid which runs from the cover proximal to the casing or outer wall of the vessel toward the bottom thereof, then inwardly toward the vessel axis and then within the inner space through the second tube bundle back to the cover with the two ends of each tube forming part of the tube bundles or at least the ends of the tube bundles proximal to the cover communicating with manifold pipes which are led outwardly from the vessel through the cover.

The outer and inner sections of the heat exchanger tubes, connected together below the partition but separated from one another in the respective tube bundles, thus lie in distinct zones of the heat exchanger, one radially outwardly from the other, and separated from one another by the cylindrical partition.

The latter opens into the interior or the vessel at its lower end while its upper end passes coaxially through and is sealed to a conduit for supplying a second fluid through the cover into the interior of the vessel to pass around the heat exchanger tube forming the tube bundles. In other words one of the manifold pipes for the tube bundles is sealed to the conduit which extends into the partition and communicates with the interior therewith while being sealingly mounted upon the aforementioned cover. Via this conduit, the partition is sealingly connected annularly to the cover. The last mentioned pipe and the conduit are coaxial so that an annular passage is formed between the conduit and the pipe.

Outwardly of the central pipe and conduit assembly, there may be provided additional manifold pipes communicating with the tube bundles, e.g. in angularly equispaced relationship, while one or more of these latter pipes may be sealed to and coaxial with further conduits sealed to the cover and conducting the second fluid into or out of the heat exchanger in the direction opposite the direction in which this fluid passes through the central conduit.

In accordance with the principles of the present invention, therefore, the interior of the vessel is subdivided internally by the cylindrical partition into a circular cross-section, axially extending inner space and into a circular-cross section annular outer space extending axially between the partition and the housing wall.

The two spaces are in communication with one another only in the region of the bottom of the vessel. In the region of the cover the partition indirectly or directly is sealed to the cover and extends into a conduit above the cover, preferably running coaxially with the cover and the vessel, forming a passage for the second fluid.

Within the spaces mentioned previously, stretches of heat exchanger tubes are provided for the first fluid. The tube stretches which terminate in the inner space, open into a manifold pipe sealed to the cylindrical conduit, this pipe communicating with a plurality of such tube stretches, e.g. to collect fluid from these stretches.

At least one but preferably a plurality of manifold pipes communicate with groups of stretches of the heat exchanger of the outer tube bundle, the manifold pipes serving for the supply and withdrawal of the first fluid while the conduits pass the second fluid in heat exchange relationship with the tubes. Each of the conduits thus surrounds with clearance a length of a manifold pipe so that a passage extends along this length for traversal by the second fluid.

The fluids are fed to and led from the heat exchanger preferably so that the so-called "hot-end" of the heat exchanger lies in the region of the axis thereof while the "cold end" lies externally of the axis. Consequently, the outer portion of the cover, all or part of the bottom, the outer conduits and the outer manifold pipes lie at the cold side.

The elements which are subject to high temperature are only the central manifold tube, the conduit for the second fluid and any further tubes which are close to this conduit. The lower ends of the latter tubes can be connected with the cold side of the cover and only reach critical temperature at the extreme upper side of the temperature range.

All of the hot and therefore critical elements have relatively small diameters in the system of the present invention.

It has been found to be advantageous, with the system of the present invention, that only a small portion of the heat exchanger is subjected to the maximum temperature and that these portions have a relatively simple geometry so that the length of the heat exchanger can be as small as possible. The heat exchanger of the invention can be subjected to high temperatures and pressures and can be produced with large dimensions. The damage which can occur at critical regions is minimized and the stress characteristics can be calculated by standard techniques.

According to a feature of the invention, the second pipe or duct, which coaxially surrounds the central manifold pipe, is in turn surrounded by a further pipe or duct, hereinafter referred as a conduit, which can be affixed to the cover of the heat exchanger.

This conduit is provided with a cooling coil. The conduit can form the hottest point of the hot end of the heat exchanger, being substantially at its upper end at the temperature of the hotter of the two fluids. The lower end of this conduit is thus fixed to the cover of the heat exchanger and is, substantially, at the temperature of the colder fluid.

Since there is practically no fluid flow in the space between this conduit and the duct lying coaxially inwardly thereof, a certain amount of heat is transferred from this duct to the conduit. The cooling coil surrounding the latter dissipates the heat on the one hand by thermal conduction and on the other hand by radiation and convection.

According to another feature of the invention, a stiffening plate is provided to reinforce the cover, the stiffening plate being spaced therefrom but rigidly connected thereto. The stiffening plate can be located within the vessel or externally thereof and can be planar or can be curved, e.g. to conform to the curvature of the cover. Similarly, the cover of the heat exchanger can be planar or curved, e.g. outwardly domed.

The connection between the cover and the stiffening plate can be effected by the ducts or conduit previously mentioned to which the stiffening plate can be welded, and/or by an upward tension of the side wall or shell of the vessel, and/or by a portion of the side wall of the vessel itself, and/or by tension members connected to the cover and the stiffening plate and spanning the gap between them. The stiffening plate takes up a portion of the pressure forces which may apply to the cover.

Because of the presence of the stiffening plate, the wall thickness of the cover can be reduced for a given nominal pressure of the vessel, thereby reducing costs of components which may have to be made from scarce or special materials.

According to yet another feature of the invention, the inner tube bundle is provided with an outer sealing sleeve or layer which can be connected with the cylindrical partition or shell to prevent a bypass flow of fluid between the shell or partition and the outer layer of helically coiled tubes of the inner tube bundle. The bypass flow of fluid would, of course, limit the heat exchange. Furthermore, between the partition and the sealing layer, a thermally insulating layer can be provided.

Similarly, the outer tube bundle may be closely surrounded and hugged by a sealing layer which is connnected with the interior of the vessel wall. Again a bypass flow of fluid is precluded. The layer may be separated from the inner surface of the outer vessel wall by a layer of thermal insulation.

It has been found to be advantageous, according to another feature of the invention, to fill the vessel at least partially with a loosely piled packing or filling of a catalytically active material, a filtering material and/or a material which promotes heat exchange by storing heat. When the material is a catalyst, it can be selected to promote a given catalyst reaction in one of the fluids.

According to yet another feature of the invention, the duct through which the manifold pipe extends centrally, has a removable cover, cap or top and a diameter dimensioned to allow withdrawal of the central manifold pipe together with the inner tube bundle. This permits inspection as required. The inner diameter of the duct thus can be at least equal to the outer diameter of the inner tube bundle and can be formed with a fitting for the second fluid. The duct thus forms a cylinder extending the partition upwardly and can be the support for the outer tube bundle while providing the passage whereby pipes or tubes extend through the cover. The cylinder can also be formed by the conduit mentioned previously, i.e. the further duct, in which case the duct coaxially centrally traversing the conduit can extend through the cylinder.

Where the conduit has the same diameter as the partition, the entire inner coil of the heat exchanger can be removed from the partition without damaging or affecting the cover of the heat exchanger. By removal of this inner coil, inspection of or addition to the packing is possible.

It has also been found to be advantageous to provide a closable opening in the bottom of the upright heat exchanger to allow the discharge of the contaminants which can collect therein and/or to permit the flow of fluid to or from one of the heat exchanger coils when the heat exchanger is to be used under less than full load.

The additional fitting in the bottom of the vessel does not involve the use of any critical materials or structures, since the hot end is always at the upper side.

As indicated earlier, the opening valve plays a twofold role. On the one side, it allows impurities to be drained from the fluid which is cooled in the heat exchanger so that these fluids can be discharged. In addition, a cold fluid can be introduced into the heat exchanger through this opening or the latter can be used to supply the cold fluid or to draw off a cooled fluid. Valves communicating with the various lines in the head or at the cover of the heat exchanger can control the direction of flow.

It has been found to be advantageous also to provide between the vessel wall and the outer tube bundle a cooling coil which lies parallel to the outer layer of coils. In this case, the manifold pipe or the outer tube bundle can be provided with a shunt line containing at least a valve and communicating via one of the valves with the feed conduit to this additional cooling coil. In general valves are provided, therefore, to allow the cooling coil to be fed in either direction independently of the direction of feed for the heat exchanger tubes of the outer space.

To facilitate anchoring the various parts to the inner wall of the vessel a plate provided with gas-traversing openings is provided across the bottom to further support the assembly formed by the coils. The feed line for the cooling coil can also be extended out of the vessel through the cylinder.

At the inlet and outlet passages the reacting fluid can be provided with filters to prevent contaminants from entering the system without material detriment to the operating efficiency. When it is desired to preclude deposits on the outer coil layer, it is advantageous to provide the partition shell as a basket which, upon withdrawal from the heat exchanger scrapes away any deposits through the basket openings. The basket shell may, of course, by surrounded by a sealing sleeve with a similar effect to the sealing action already described when the basket is in place. The heat exchanger of the present invention has been found to be especially effective when used as a methane synthesis reactor for the production of methane from synthesis gas by the strongly exothermic reaction In this case a nickel-containing catalyst may form the packing.

Another aspect of the invention resides in the method by which the heat exchanger is formed. The common practice heretofore was to provide coil-tube heat exchanger in a single operation for forming all of the coils around a core tube. The limit in the size in the heat exchanger made in this manner was 70 to 120 tons. The core tube was rotatably mounted and rotated as the coils were wound thereon. When the heat exchanger reached the maximum permissible weight, in the above-stated range, the coiling was terminated just prior to buckling of the core tube.

Naturally, the resistance to buckling could be increased by increasing the diameter of the core tube but results in an increase in the useless volume. According to the present invention, the problems are avoided by simultaneously coiling the inner tube bundle on its core tube and the outer coil bundle on the partition, shipping the two tube bundles separately to the erection site and then sliding the outer tube bundle over the inner tube bundle into the outer tube bundle to assemble the heat exchanger. Thus even if each tube bundle has a weight of less than 150 tons, the practical maximum for convenient shipping, the total mass of the heat exchanger can far exceed 150 tons when the two heat exchangers are assembled and are interconnected below the partition.

BRIEF DESCRIPTION OF THE DRAWING

The above and other objects, features and advantages of the present invention will become more readily apparent from the following description and specific Examples, reference being made to the accompanying drawing in which.

SPECIFIC DESCRIPTION AND EXAMPLES

The present invention is described below in terms of heat exchangers for various purposes and a best mode process which can be carried out with the high-temperature, high-pressure heat exchangers of the invention, e.g. coal gasification with a pressurized-water reactor or methane synthesis.

In such a heat exchanger the heat content of the coal gasification reaction gases can be transferred to steam generated in a nuclear reactor and the operating pressure at both sides can be about 60 bar. The temperature at the hot end of the heat exchanger can be between 900° and 1250° K. and the efficiency of the apparatus increases with increasing temperature and increasing pressure of the reactor steam sides. The reactor steam can be at a temperature of 500° to 600° K.

Figure 1:
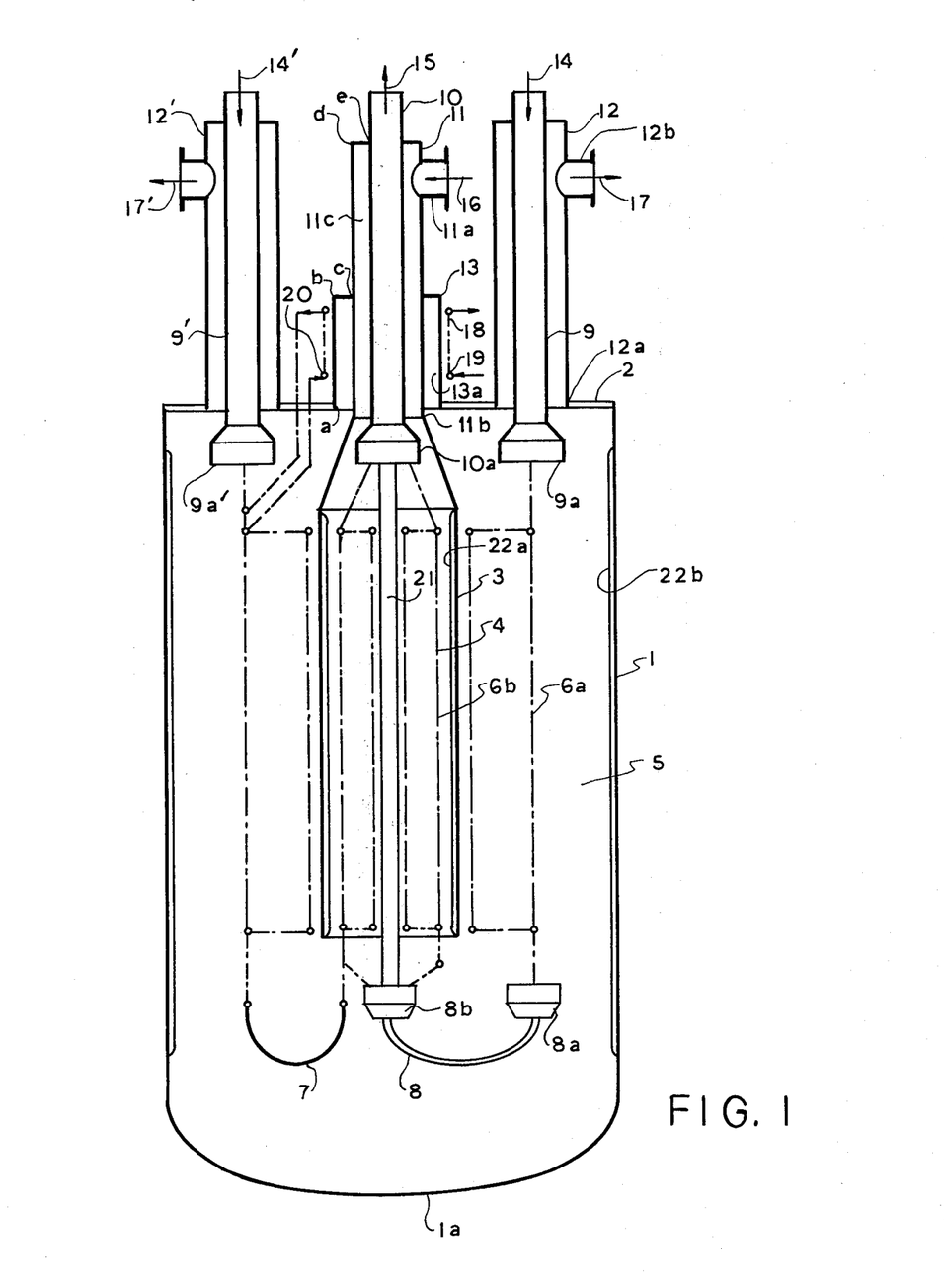
FIG. 1 is a vertical cross-sectional view through a heat exchanger according to the invention in diagrammatic form.

The heat exchanger illustrated in FIG. 1 comprises a cylindrical vessel or shell 1, with a vertical principal axis, which is closed at its bottom 1a.

At its upper end, the casing or shell 1 is closed by a cover 2 which has been represented only diagrammatically. In practice, the cover 2, which can be flat or upwardly convex (domed) will be provided with a peripheral flange which embodies the cover to be removable bolted to the outwardly extending peripheral flange on the housing. Such flanged attachments of the cover to the casing are, of course, well-known in the art. A weld closure can also be used.

Within the interior of the vessel formed by the cover 2 and the casing 1, there is provided a cylindrical shell or partition 3 which is fixed to the cover and extends downwardly therefrom to terminate at a location close to but spaced from the bottom 1a of the vessel 1.

The cylindrical partition 3 thus subdivides the interior of the vessel into a circular-section inner space 4 and a circular section annular outer space 5. The two spaces 4 and 5 are interconnected below the lower end of the partition 3.

The spaces 4 and 5 into which the interior of the vessel is subdivided receive heat exchanger tubes 6a and 6b respectively which depend from and are attached to the cover 2, the heat exchanger tubes 6a and 6b being in communication below the lower end of the partition as will be developed in greater detail below.

The heat exchanger tubes 6a and 6b may each form part of a tube bundle which can be of the helical-coil close-packed type, can be spirally-coiled heat exchanger tubes or can be axially extending rectilinear heat exchanger tubes or any combination thereof. Reference may be had to the U.S. Pat. No. 4,084,546 which also shows a configuration of both rectilinear or coiled-tube bundles which may be applied for the present purposes.

In general a single flow path through these tubes proceeds from the cover 2 generally along or parallel to the outer wall of the vessel in the direction of the bottom, then inwardly toward the vessel's axis and within the partition 3 upwardly to the cover 2.

As has been stated, the heat exchanger tubes are assembled into tube bundles which can be coiled around the partition 3 in the outer space 5 and coiled around a core tube 21 within the inner space 4. Coiling arrangements of this type have been illustrated in U.S. Pat. No. 4,084,546 and need not be described in greater detail. A coiled-tube heat exchanger of this type provides excellent heat transfer and a highly specific surface (heat transfer surface per unit volume) so that the heat transfer is optimized for a given volume and weight of the heat exchangers.

While the type of winding will depend upon the requirements for a particular heat exchanger, e.g. as to pitch, coiled-tube diameter, density of coiling, etc., in general a plurality of tubes should lie in each helical layer and a plurality of helical layers should be provided as illustrated in the last-mentioned patent. Naturally, some of the tubes may run rectilinearly through one or both of the spaces 4, 5 preferably in combination with coil tubes, e.g. between layers thereof, or rectilinear tubes can be used to the exclusion of coiled tubes. The desired fluid path length for the requisite heat transfer will, of course, determining the configuration of the tube bundles or each tube bundle. The preferred and best mode, of course, is the helical-coil configuration which has been represented only diagrammatically in the drawings since individual delineation of each of the many tubes and many tube turns involved in such a helical-coil tube bundle would obscure other aspects of the invention.

The tubes can run continuously through the two spaces, i.e. can be formed in one piece and can be bent below the partition from the descending stretch in space 5 to the ascending stretch in space 4 as has been diagrammatically shown by the bend 7 in FIG. 1.

However, it is preferred to provide the tubes 6a and 6b separately from one another and to collect a number of tubes 6a in the space 5 into groups with each group communicating with a manifold 8a connected via a duct 8 with another manifold 8b communicating with a corresponding group of tubes extending through space 4. This has also been illustrated in FIG. 1.

In either case, the communication between the tube stretches 6a and 6b permits compensation for stresses resulting from the temperature differences in the tube sections 6a and 6b, i.e. expansion of the respective tube bundles or relative movement thereof. At their upper ends, the tubes 6a communicate with manifold pipes 9, 9' which can be angularly equispaced about the axis of the vessel and run through the cover tube from their respective manifolds 9a and 9a'. The number of manifold pipes 9, 9' will, of course, depend upon the operating requirements, especially the flow volume to traverse the heat exchange tubes.

The inner tubes 6b open into a centrally disposed manifold pipe 10 at its manifold 10a. The central manifold pipe 10 also extends through the cover 2. The central manifold pipe 10 defines an annular passage with a coaxial second tube or duct 11 provided with a fitting 11a which can be flanged to a source of the hot reaction gas. The duct 11 is sealed at its lower end 11b to the cylindrical partition 3 and can form a unit therewith whereby the hot reaction gas is fed through the annular space 11a downwardly and then through the inner space 4 to pass below the bottom of the partition 3 and thence upwardly through the outer space 5.

Coaxial with the manifold tubes 9 and 9' are further ducts 12 and 12', respectively, which are sealed at the lower ends 12a to the cover 2 and are formed at their upper ends with fittings 12b enabling them to be connected to a pipe system for discharging the cold reaction gas in the direction of arrow 17. Arrow 16 represents the direction of feed of the hot reaction gas.

The duct 11 coaxially surrounding the central manifold pipe 10 is, in turn, coaxially surrounded by a further conduit 13 which defines an annular space 13a therewith communicating with the outer space 5 of the vessel.

In the present specific example, reactor steam at a temperature 500° K. to 600° K. is introduced as represented by the arrows 14 and 14' through the manifold pipes 9 and 9' to the heat exchanger tubes 6a and 6b and the superheated steam recovered at 15 has a temperature at 850° K. to 1200° K. at the central manifold pipe 10.

The hot reaction gas is introduced at 16 at a temperature of 900° K. to 1250° K. through the central second pipe or duct 11 and is cooled by heat exchange with the reactor steam leaving the heat exchanger in the direction of arrow 17, 17' at a temperature of 550° K. to 700° K.

Naturally it is also possible to alter the direction in which the fluids are fed through the system. For example, the hotter fluid can be supplied through the central manifold pipe 10 while the colder fluid is fed through the ducts 12 and 12' whereby the hot end of the heat exchanger in the region of the axis of the vessel whereas, in the arrangement described earlier, the "hot end" lies outwardly of the axis.

It has been found to be advantageous, in either case, to pass the reaction gas through the spaces 4 and 5 direction, i.e. to avoid passing the reaction gas through the heat exchanger tubes 6a and 6b because the reaction gas, in the present specific example, generally contains soot and dust particles which then deposit upon the inner walls of the heat exchanger tubes and cause corrosion or encrustation which may even block the flow cross section.

A cooling coil 18 is provided around the further pipe (conduit) 13 and can be fed either with a third fluid as represented by the arrow 19 or by the colder of the two fluids which as passed in heat exchanging relation as represented by the arrow 20. This cooling coil has also been represented in highly diagrammatic form so as not to obscure other elements of the structure.

The inner and outer sections 6a and 6b of the heat exchanger pipes in contact with sealing layers 22a and 22b (see FIG. 1A) to prevent passages from being formed along the outer helical layers of the respective tube bundles between these outer lines and the wall of the vessel 1 or the partition 3 through which the gases traversing the spaces 4 and 5 can flow without proper heat exchange.

Figure 1A:
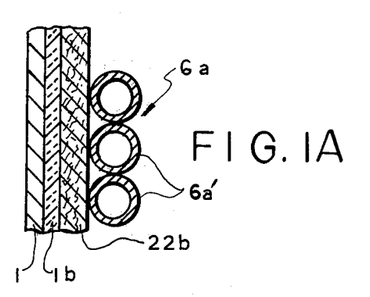
FIGS. 1A and 1B are detail views illustrating features of the invention, the views being in cross section.

In FIG. 1A, the outer layer of heat exchanger tubes is represented at 6a' and is shown to be in engagement with the sealing lining 22b. Thus any flow of gas between the layer 6a' and the wall 1 is precluded. The lining 22a operates similarly.

Between the outer lining 22b and the vessel wall there may be provided a layer of thermal insulation as has been illustrated at 1b in FIG. 1A. The insulation can, however, extend over the entire wall of the vessel 1. Similarly, between the partition 3 and the sealing layer 22a a layer of thermal insulation can be provided if desired or required.

To facilitate an understanding of the operation of the heat exchanger, particularly as to which of its structural elements may be the critical temperatures and pressures, it is pointed out that within the vessel 1, for which the cover 2 provides the sole access and egress for fluids, the pressure is about 60 bar and is practically equal both within the spaces 4 and 5 and within the tubes and ducts.

The pipes 9,9' and duct 11 which feed fluids to the heat exchanger, the pipe 10 and the ducts 12, 12' which conduit fluid from the heat exchanger, the vessel 1, the cover 2 and the further duct or conduit 13 must all be capable of withstanding this pressure. Similarly the heat exchanger tubes 6a, 6b traversed by the steam from the nuclear reactor, must be capable of withstanding this pressure. Since the same pressure is applied on both sides of the partition 3, this partition need not be constructed so as to be capable of withstanding such high pressures.

The highest temperatures in the heat exchanger are found at the manifold pipe 10, in the duct 11 and in the upper part of the further duct or conduit 13. These components can be made from high-quality, refractories and low corrosion steel alloys, for example, IN-COLOY. Because of the provision of the cooling coils 18 and its large heat transfer cross section with the cover 2, the conduit 13 has a negative temperature gradient downwardly. The space between duct 11 and the conduit 13 is filled with the reaction gas.

Because of this annular compartment and the cooling winding, the cover 1 is larger thermally isolated from the hot duct 11. The radial thickness of the annular space should not, however, be so great that gas turbulence can occur therein.

In addition, to improve the thermal insulation, an insulating material can be introduced into the annular space.

Figure 1B:
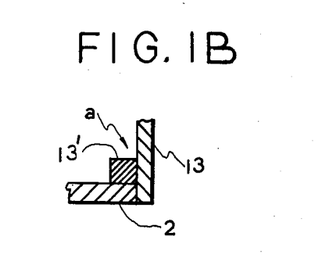

At the locations a, b, c, d and e annular reinforcement is provided as represented at 13' FIG. 1B to stiffen these high-stress areas.

The portions of the unit especially susceptible to the corrosion within the partition 3 are easily accessible. Since the same pressure applies on both sides of the partition and the net pressure on this partition is minimized by the fact that it does not constitute an enclosure to which a pressure gradient is applied, the partition can easily be cut away and welded back again in place for the access mentioned.

Figure 2A:
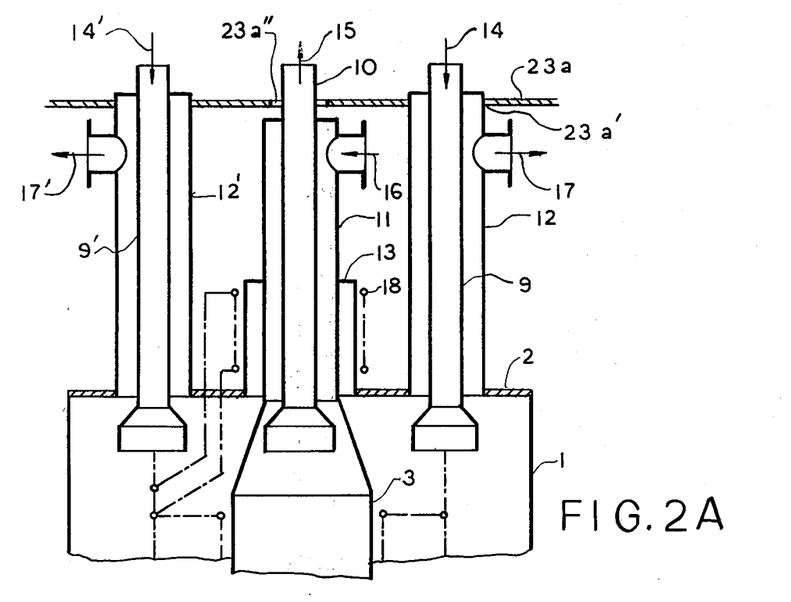
FIGS. 2A through 2E are vertical cross-sectional views through embodiments of the invention showing only the upper end of the heat exchanger and the arrangements of the conduits and ducts at the upper end.

In the embodiment of FIG. 2A, the stress upon the cover 2 is relieved in part by the provision of a stiffening plate 23a which may be welded at 23a' to the outer ducts 12, 12'.

In FIGS. 2A through 2E, similar parts have the same reference numerals and the reference numerals are the same as those used for corresponding parts in the embodiment of FIGS. 1, 1A and 1B.

In all of FIGS. 2A through 2E, the stiffening plate has approximately the same temperature as the fluid at the cool side of the heat exchanger.

For example, this is achieved by welding the plate 23a to the ducts 12 and 12' while providing a clearance 23a" through which the manifold pipe 10 passes.

Figure 2B:
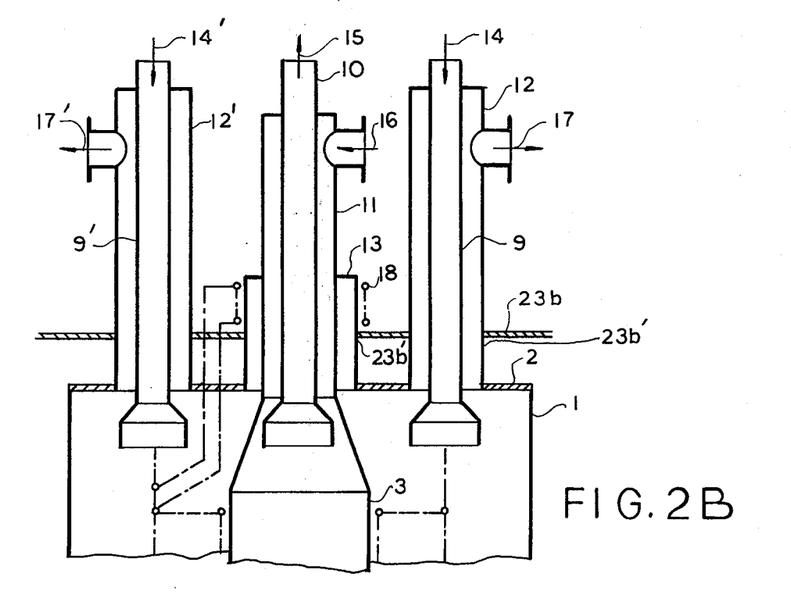

In the embodiment of FIG. 2B, the stiffening plate 23b is disposed closer to the cover 2 and is welded at 23b' not only to the outer ducts 12 and 12' but also to the further duct or pipe 13 which, however, is cooled by the coil 18. The stiffening plate 23b is here located below the cooling coil although it may also be provided directly thereabove and can be similarly connected to the ducts 12, 12' and 13. The additional connection of the stiffening plate 23b to the further duct 13 has the advantage that the bending stress upon the cover 2 is reduced.

Figure 2C:
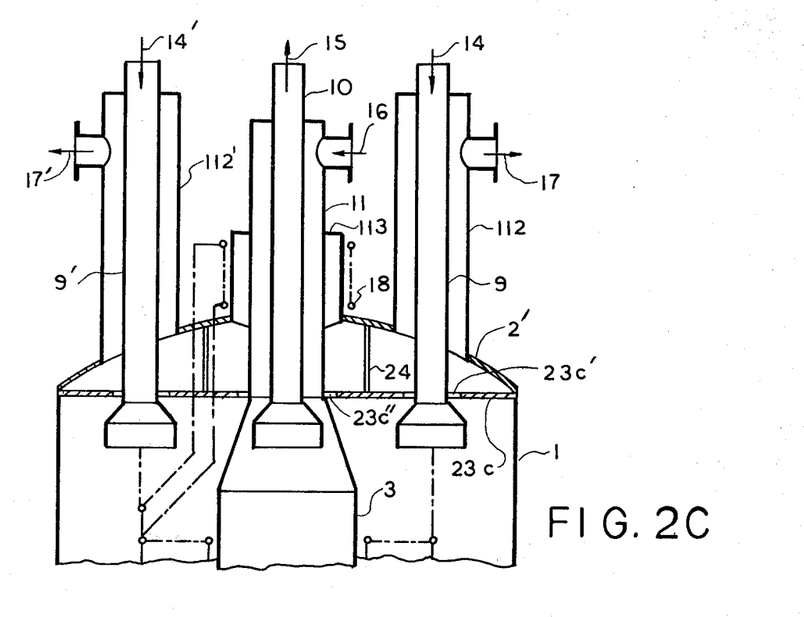
Figure 2D:
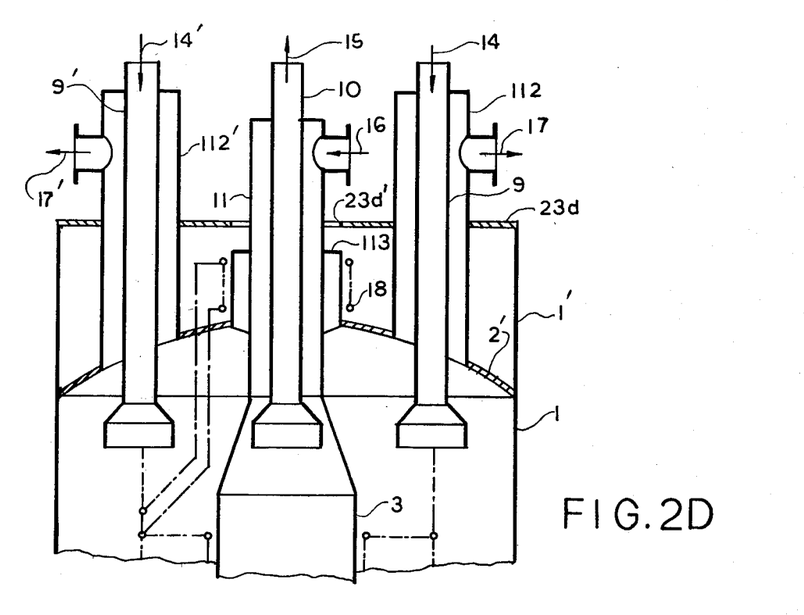

FIGS. 2C and 2D show embodiments in which a domed cover 2' is combined with a planar stiffening plate 23c or 23d.

In FIG. 2C, therefore, the outwardly and upwardly convex domed cover 2' is affixed to the ducts 112 and 112' in the manner previously described and to the further duct 113.

In this case, the planar stiffening plate 23c is formed with openings 23c' which are traversed by the manifold pipes 9 and 9' and a central opening 23c" clearing the duct 11. The plate 23c is connected to the vessel wall 1 and, via tension rods 24, with the cover 2'. The openings 23c' and 23c" can permit the reaction gas to pass into the space between the cover 2' and the plate 23c, i.e. into the space surrounded by the further duct 113.

In the embodiment of FIG. 2D, however, the cover 2', which is connected with the ducts 112, 112' and 113 in the manner described in connection with FIG. 2C, cooperates with a stiffening plate 23d which is located above the cover 2' and possibly at a region above the top of the further duct 113. Here, therefore, the stiffening plate 23d has an opening 23d' which passes the duct 11 with clearance. The plate 23d is welded to the ducts 112, 112' and to a vertical extension 1' of the vessel wall 1.

Still other modifications of such structures can be provided combining features of FIGS. 2A through 2D. For example, the wall extension 1' can be used in the embodiment of FIGS. 2A and 2B in which the stiffening plate is located above the cover and can be welded to such cover plate.

Figure 2E:
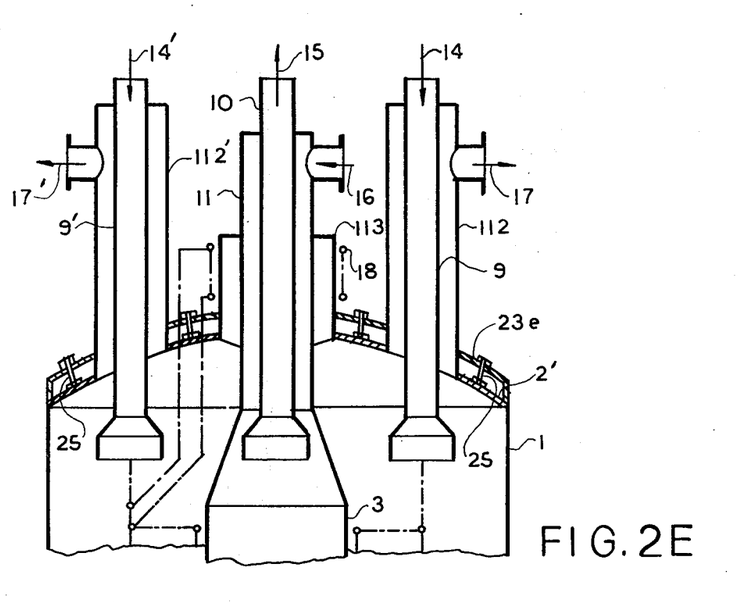

In the embodiment of FIG. 2E, the stiffening plate 23e is upwardly convex, i.e. is upwardly and outwardly domed, being mounted above the cover 2' to which it is connected by bolts 25 as has been shown diagrammatically in this FIGURE. The plate 23e can, of course, be welded to the ducts 112, 112' and 113.

Figure 3:
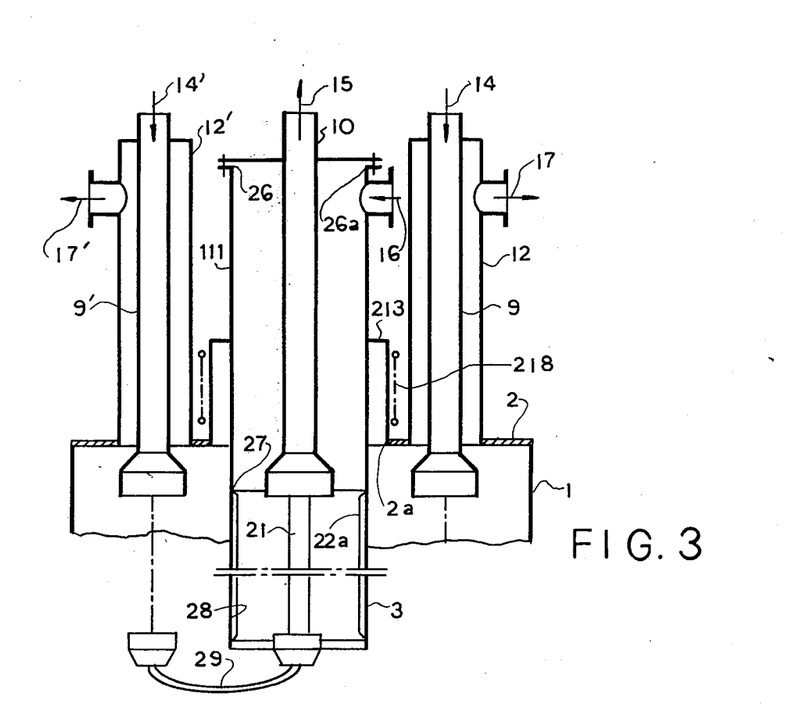
FIG. 3 is a vertical cross-sectional view, also in diagrammatic form, illustrating a further modification in accordance with the present invention.

In FIG. 3, I have shown a further embodiment of the heat exchanger of the present invention wherein, deviating from the previous embodiment, the central duct 111, which coaxially surround the manifold pipe 10, has the same diameter as the partition 3. This will generally require a larger opening 2a in the cover 2 and hence a larger diameter further duct or conduit 213, as well as a larger diameter cooling coil 218.

The entire assembly 111 with its sealing layer 22a and the manifold pipe 10 (with or without the associated tube bundle) can be withdrawn from the heat exchanger, cleaned and replaced or simply exchanged for a corresponding unit.

According to another aspect of the invention, the upper closure member 26a of the duct 111 may have a removable connection as represented by the flange joint 26, to enable this member 26a to be removed. The manifold pipe 10 can then be withdrawn with the inner tube bundle for cleaning, maintenance or replacement. The connection between inner and outer tube sections can be separated by opening welds at locations 27, 28 and 29. Furthermore, a simple weld can be provided at 26, in place of the removable connection, if desired, this weld being burned away to allow disassembly of the heat exchanger.

It has been found to be especially advantageous (see FIG. 4) to mount a metal cylinder 30 upon the vessel 1, and to pass this relatively large diameter cylinder through an opening in the cover 202. The cylinder 30 can be provided with a fitting 312b through which the reactor gas is discharged. In this embodiment, the coil 318 surrounds a cylindrical extension 313 of the cylinder 30 which is extended by a partition 303 and which is closed at its bottom by a frustoconical transition piece 311' communicating between the inner space 304 and the central duct 311. The central duct 311 has the fitting 311a into which the hot reactor gas is introduced in the direction of arrow 16.

Figure 4:
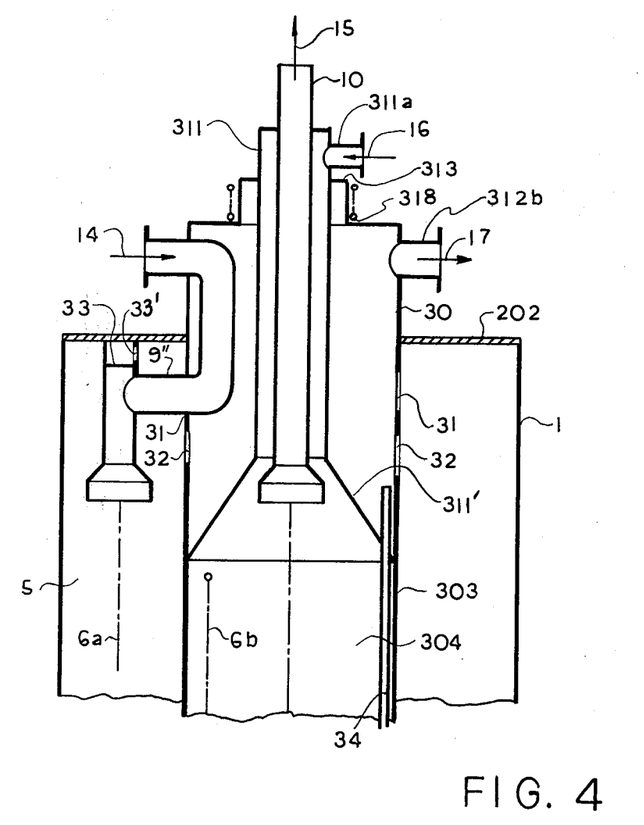
FIG. 4 is a view similar to FIG. 3 illustrating another embodiment of the invention.

The central manifold pipe 10 is connected to the inner tube bundle, i.e. the tubes 6b, in the manner previously described. In this embodiment the diameter of the further duct 313 should be at least equal to the diameter of the outermost coil of the inner tube bundle of the tubes 6b.

In this embodiment, the diameter of the further pipe 313, which has a high temperature upper end, can be substantially smaller while nevertheless permitting replacement of the inner tube bundle.

The cylinder 30 is extended with uniform diameter to the partition 303 and serves as suspending device for this partition and for the outer tube bundle. In the region between the cylinder 30 and the partition 303, openings 31, 32 are provided to allow fluid to pass into the cylinder. The openings 31, 32 also have the advantage that they allow access to internal elements of the system for maintenance.

The cylinder 30 also serves as a support for the manifold pipe 9" for the reaction steam and also has, as has been indicated, the fitting serving as the reaction gas outlet. As a result, additional fittings, openings or formations on the vessel cover 202 need not be provided.

Naturally, it is also possible to provide the bundle of outer tubes 6a with its manifold pipe 9" in such configuration that it is suspended independently from the vessel cover 202. In this case, the manifold pipe can have a T configuration with its straight head running to the cover 202 and there being suspended. The fluids thus flow through this manifold pipe via the branch. Such an arrangement has been illustrated in 33 where a cover is provided in the T-shaped pipe to prevent exposure of the cover 202 to the pressure and temperature of the fluid in the heat exchanger tubes. The pressure equalization bore 33' can be provided between the interior of the partition pipe section and the outer space 5 of the vessel. The cover 202 thus has a uniform pressure over its entire inner surface. When, however, it is not important to prevent application of the heat or pressure of the fluid traversing the heat exchanger tubes to the cover, the partition 33 and the pressure-equalization port 33' can be eliminated.

In the embodiment of FIG. 4, the reaction gas is admitted at 16 and leaves the heat exchanger via the cylinder 30 in the direction of arrow 17. The flow of the heat exchange fluid, e.g. steam, through the system is represented by the arrows 14 and 15.

In all of the embodiments of heat exchangers in accordance with the present invention, the vessel 1 can contain a packing or filling of catalyst material or a material promoting heat exchange.

Figure 5:
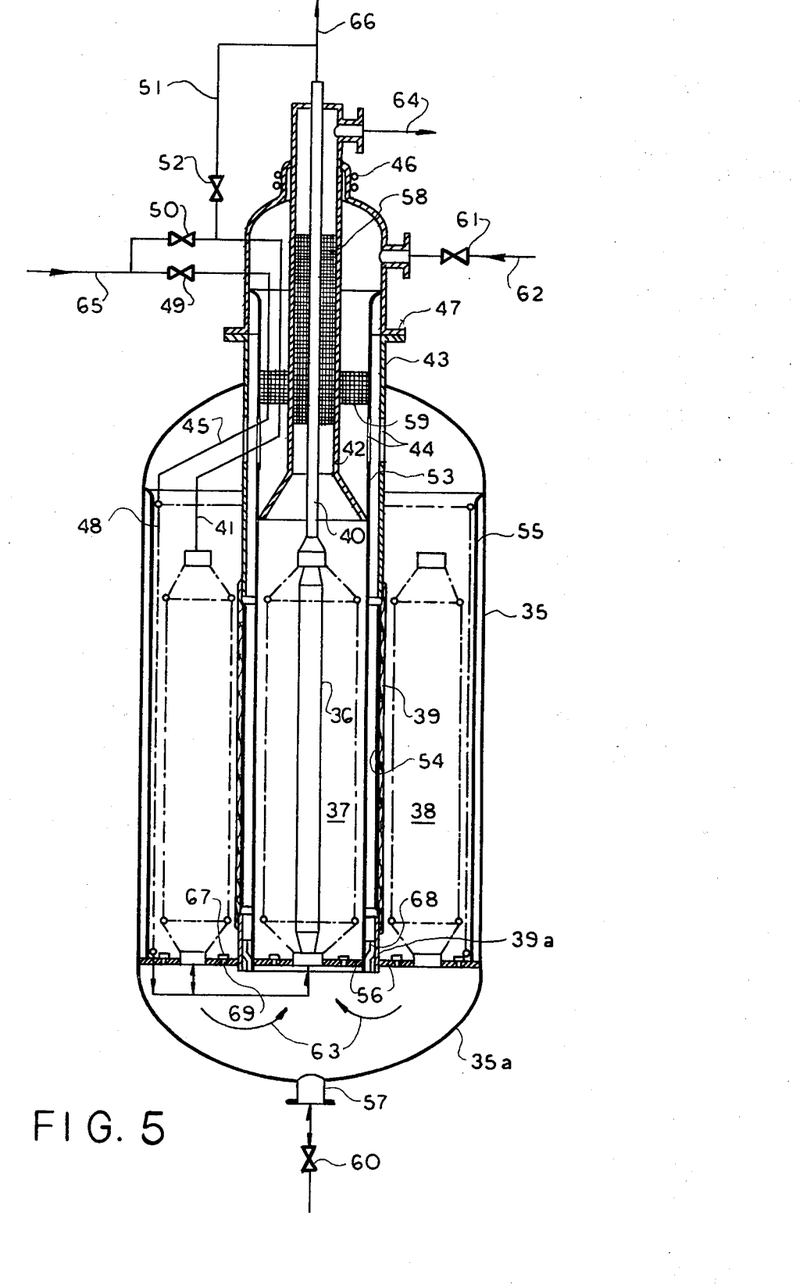
FIG. 5 is a vertical diagrammatic section through yet another embodiment of the invention but showing the entire heat exchanger.

The heat exchanger shown in FIG. 5 has been found to be especially effective for the synthesis of methane from carbon monoxide and hydrogen, i.e. from socalled synthesis gas.

This reactor comprises a cylindrical vessel 35 containing two concentric (coaxial) helical-coil tube bundles with the inner coil 37 being wound around a core tube 36 while the coils of the outer tube bundle 38 are wound around a cylindrical shell 39.

The shell 39 is advantageously formed of a basket weave or open work construction and is mounted upon a support ring 39a to permit access to the outer tube bundle 38.

The tube bundles 37 and 38 can have the configuration illustrated in the aforementioned patent.

The tube bundles 37 and 38 are interconnected at their underside as represented diagrammatically in FIG. 5 so that fluid can continuously flow through the heat exchanger tubes in one tube bundle and then below the partition and through the heat exchanger tubes of the other tube bundle in the opposite direction.

The free ends of the coils communicate with manifold pipes. 40, 41 which extend out of the reactor or vessel 35.

Between the central manifold pipe 40 and the interior of the shell 39, there is provided the duct 42 which sealingly communicates with the interior of the shell 39 and is of a smaller diameter than the inner space defined thereby. The inner space thus communicates, as represented by arrows 63, with the outer space of the vessel.

The annular space between the shell 39 and the wall of the vessel is connected via a further duct 43 with the exterior. This connection is effected by openings 44 above the tube bundles in the duct 43 and in a further duct 53 which will be described below and which serves as a sealing member and partition in the manner previously described. As can be seen from the left-hand side of FIG. 5 diagrammatically, the openings 44 also serve to pass a pipe 45 connected to a further cooling coil 48 and a pipe extending from the manifold pipe 41 to the exterior. This avoids the need for unnecessary weld seams in the cover or walls of the heat exchanger and increases the safety factor at the high temperatures and pressures in which the system operates.

Since the duct 43 has substantially the same diameter as the shell 39, the entire inner tube bundle can be removed upon release of the flange connection 47 between the upper dome and the duct 43.

The portion of the duct 43 at the hot end of the heat exchanger is cooled by the coil 46.

Between the outer tube bundle 38 and the vessel wall, the aforementioned further cooling coil 48 can be parallel to the outer layer of turns of the outer tube bundle. Valves 49 and 50 serve to control the feed of the coolant to the outer tube bundle and the coil 48 independently so that either flow can be blocked independently of the other, the cooling fluid being supplied via the line 65.

A bypass line 51 with its selectively controlled valve 52 connects the inlet to the outer tube coil 38 with the outlet of the inner tube bundle 37.

The inner tube bundle is surrounded by the sealing partition member 53 which prevents the passage of fluid between the outer layer of tubes and the partition.

The space within the basket-forming shell 39 is sealed by the cylindrical sealing member 54 from the space between the shell 39 and the wall of the vessel. Between the cooling coil 48 and the wall of the vessel, a further sealing shell 55 is provided at the upper outwardly turned lip which engages the wall of the vessel. A sealing lip 68 seals the annular gap between the support ring 39a and the partition 53.

At a distance from the outwardly and downwardly convex bottom 35a of the vessel, there is provided a plate 56 perpendicular to the axis of the heat exchanger, this plate being formed with gas-passing openings 69 of which only one has been shown in the drawing. The plate 56 serves as a support for the catalyst packing or filling loosely dumped into the heat exchanger. For the production of methane from synthesis gas, the catalyst can be constituted by nickel granules.

To prevent the catalyst from passing through the openings 69, the openings are covered by narrow-mesh screens 67.

Screen-type filters 58 and 59 are provided in the inlet and outlet flow cross sections for the gas to retain impurities.

According to the invention, moreover, the bottom of the heat exchanger is provided with a fitting 57 which may be opened or closed by the valve 60. The fitting 57 enables impurities separated below the plate 56 at the bottom of the vessel 35 to be emptied or, where necessary, permits the introduction of a fluid or removal of a fluid when the heat exchanger is to be operated at a fraction of its normal loading.

With full load operation, however, the opening 57 is closed by valve 60 while the inlet valve 61 is opened to permit the gas, i.e. a mixture of carbon monoxide and hydrogen, to flow into the duct 43 and thence via the opening 44 in the latter, through the outer annular space of the heat exchanger past the outer tube bundle 38 undergoing a catalyzed reaction to produce methane. In the filter 59, which is located upstream of the openings 44, contaminants are removed.

The products of the reaction are methane and water. The reaction heat is taken up by the coolant traversing the heat-exchanger tubes, this coolant being preferably water.

The methane flows through the plate 56 and then, as represented by the arrows 63, upwardly through the inner space within the partition where previously unreacted carbon monoxide and hydrogen react to produce methane and water vapor. The gases then leave the reactor through the central duct 42, being filtered at 58. Further reaction heat is removed in the inner tube bundle. For partial-load operation of the heat exchanger, valve 61 is closed and valve 60 is opened. The synthesis gas is then supplied through the fitting 57 and transverses only the inner space while undergoing reaction in the manner described. Naturally, by both partial load or full load operation, a reverse flow of the gas is possible. This reverse flow process is preferred when the synthesis gas is supplied in a hot state. However, for maximum advantage of the heat exchanger of the present invention, the hot end should be at 64.

The cooling fluid traversing the heat exchanger tube will, of course, flow in the direction best suited for the operation of the heat exchanger as determined by the settings of the valves 59, 50 and 52, either upwardly or downwardly through the outer heat exchanger coil and in a corresponding direction through the inner heat exchanger tube bundle. The same applies to the flow through the coil 48.

In one case, valve 50 is closed and valves 49 and 52 are opened. The cooling fluid then passes downwardly through the cooling coil 48 and downwardly in the outer tube bundle but upwardly in the inner tube bundle with the coolant from the inner tube bundle thereafter flowing through the coil 48 at least in part. In another case, valve 52 is closed and valves 49 and 50 are opened. In this arrangement the cooling fluid in the outer tube bundle 38 flows downwardly while the flow of coolant in the outer coil 48 is from the original source rather than the inner tube coil. Naturally the valve arrangements can be used for reversal of either flow direction through the cooling tubes or the heat exchanger tube bundles.

The heat exchanger shown in FIG. 5 has been used effectively in the isothermal synthesis of methane, the term "isothermal" being used to refer to the fact that the cooling water is converted to steam at constant temperature. The pressure of the synthesis gas introduced as water and steam is recovered at a pressure of 100 bar and a temperature of 600° K.

As indicated previously, the heat exchangers of the present invention can be produced by an improved process which allows larger heat exchangers to be fabricated more economically than has hitherto been the case.

Basically, each heat exchanger comprises four parts, an inner helical-coil tube bundle, an outer helical-coil tube bundle, a cylindrical vessel with a cover and a vessel bottom with a support frame although the latter has not been shown here. These elements can be separately transported to ensure that large heat exchangers can be produced with a total mass or volume exceeding normal transport availability.

At the erection site, the heat exchanger bottom with its support frame is positioned and a column plate is introduced to facilitate mounting. The inner coil with its sealing partition is then set on the mounting plate and thereafter the outer coil is applied, preferably with its sealing cylindrical member by displacing it axially over the inner coil so that the core of the outer coil is formed by the partition between the two coils. Then the vessel wall is set over the outer coil and welded to the bottom. The inner coil, the outer coil and the partition are then connected to the cover, the mounting plate is removed, and the inner sealing sleeve is connected with the partition while the outer sleeve is connected with the vessel wall. The heat exchanger tubes of the two tube bundles are then interconnected below the partition.

When it is desired to avoid providing openings in the vessel bottom to permit insertion of the mounting plate or its removal, a somewhat different modus operandi is used.

First the partition is set up with a welded bottom and simultaneously the inner and outer coils are axially telescoped and connected together. The duct 34 (FIG. 4) is then arranged parallel to the core tube and can extend the full length of the tube bundles. Water is poured into the vessel bottom and frozen and the coils are lowered into the vessel bottom and frozen and the coils are lowered into the vessel 1 onto the ice surface. The cover 2 is then set in place and connection between the ducts, papers and tubes is made so that the coils are suspended from the cover. The water is then melted and aspirated out of the system through the duct 34 which is thereafter closed.

I claim:

1. A heat exchanger comprising:
 a closed axially elongated cylindrical vessel formed at one end with a cover and at the other end with a bottom;
 a cylindrical partition extending from said cover toward said bottom and terminating short of said bottom while subdividing the interior of said vessel into a cylindrical space within said partition and a cylindrical outer space surrounding said partition, said spaces communicating with one another between an end of said partition and said bottom;
 an inner tube bundle in said inner space and an outer tube bundle in said outer space, said inner and outer tube bundles being each formed by a multiplicity of heat exchanger tubes;
 means connecting the tubes of said outer bundle with tubes of said inner bundle between said end of said partition and said bottom;
 a central manifold pipe connected to the tubes of said inner tube bundle and at least one further manifold pipe connected to the tubes of said outer tube bundle, said manifold pipes passing through said cover for feeding a first fluid to and removing said first fluid from said tube bundles whereby said fluid passes through said tube bundles in succession; and
 a central duct coaxially spacedly surrounding said central manifold pipe externally of said vessel and communicating with said inner space, and at least one further duct spacedly surrounding coaxially a respective said further manifold pipe and communicating with said outer space for passing a second fluid through said spaces in succession, said ducts communicating with said spaces through said cover whereby all fluid feed to said tubes and spaces and all fluid discharged from said tubes and said spaces is effected through said cover.

2. The heat exchanger defined in claim 1, further comprising a stiffening plate spaced from said cover and rigidly connected therewith.

3. The heat exchanger defined in claim 1, further comprising a sealing layer interposed between said partition and said inner tube bundle and connected with said partition.

4. The heat exchanger defined in claim 1, further comprising a sealing layer formed on the wall of said vessel and engaging said outer tube bundle.

5. The heat exchanger defined in claim 4, further comprising a layer of insulation between said sealing layer and said wall of said vessel.

6. The heat exchanger defined in claim 1, further comprising a mass of a packing permeable to gas flow in at least one of said spaces.

7. The heat exchanger defined in claim 6 wherein said packing is a catalyst for a reaction to be conducted in said spaces.

8. The heat exchanger defined in claim 1 wherein said conduit is a cylinder extending to said partition and forming said further duct, said cylinder having an inner diameter at least equal to the outer diameter of said inner tube bundle and said further manifold pipe extending out of the heat exchanger at least in part through said cylinder.

9. The heat exchanger defined in claim 8 wherein said outer tube bundle is suspended from said cylinder.

10. The heat exchanger defined in claim 1 wherein said bottom is formed with a closable fitting.

11. The heat exchanger defined in claim 1, further comprising an additional cooling coil disposed between said outer tube bundle and the wall of said vessel, and connected in parallel with the outer tube bundle, the manifold pipe of the outer tube bundle being connected via a closable bypass line with manifold pipe of the inner tube bundle whereby the additional cooling coil and the feed to the outer tube bundle can be closed off independently from one another.

12. The heat exchanger defined in claim 1, further comprising a support plate extending across said vessel between the bottom and said end of said partition, said support plate being provided with gas-permeable openings.

13. The heat exchanger defined in claim 1, further comprising filters along said ducts for removing contaminants from said second fluid.

14. The heat exchanger defined in claim 1, wherein said partition is formed at least in part as a basket, further comprising a sealing sleeve surrounding said basket.

15. A method of making a portion of the heat exchanger defined in claim 1 which comprises separately coiling the inner tube bundle and the outer tube bundle on a tube core and on said partition, respectively, and then telescopingly interfitting said tube bundles and interconnecting the tubes thereof beyond the end of said partition.

16. The heat exchanger defined in claim 1 wherein each of said tube bundles comprises a multiplicity of layers of helically coiled tubes each of said layers having a plurality of such tubes.

17. A heat exchanger comprising:
 a closed axially elongated cylindrical vessel formed at one end with a cover and at the other end with a bottom;
 a cylindrical partition extending from said cover toward said bottom and terminating short of said bottom while subdividing the interior of said vessel into a cylindrical inner space within said partition and a cylindrical outer space surrounding said partition, said spaces communicating with one another between an end of said partition and said bottom;

an inner tube bundle in said inner space and an outer tube bundle in said outer space, said inner and outer tube bundles being each formed by a multiplicity of heat exchanger tubes;

means connecting the tubes of said outer bundle with tubes of said inner bundle between said end of said partition and said bottom;

a central manifold pipe connected to the tubes of said inner bundle and at least one further manifold pipe connected to the tubes of said outer tube bundle, said manifold pipes passing through said cover for feeding a first fluid to and removing said first fluid from said tube bundles whereby said fluid passes through said tube bundles in succession;

a central duct coaxially surrounding said central manifold pipe and communicating with said inner space, and at least one further duct communicating with said outer space for passing a second fluid through said spaces in succession, said ducts communicating with said spaces through said cover;

a conduit fixed to said cover and coaxially surrounding said central duct;

a cooling coil surrounding said conduit, said conduit being a cylinder extending to said partition and forming said further duct, said cylinder having an inner tube bundle; and a supply line for said cooling coil extending out of said vessel through said cylinder.

18. The heat exchanger defined in claim 17, further comprising a stiffening plate spaced from said cover and rigidly connected therewith.

19. The heat exchanger defined in claim 17, further comprising a sealing layer interposed between said partition and said inner tube bundle and connected with said partition.

20. The heat exchanger defined in claim 17, further comprising a sealing layer formed on the wall of said vessel and engaging said outer tube bundle.

21. The heat exchanger defined in claim 20, further comprising a layer of insulation between said sealing layer and said wall of said vessel.

22. The heat exchanger defined in claim 17, further comprising a mass of a packing permeable to gas flow in at least one of said spaces.

23. The heat exchanger defined in claim 22 wherein said packing is a catalyst for a reaction to be conducted in said spaces.

24. The heat exchanger defined in claim 17 wherein said bottom is formed with a closable fitting.

25. The heat exchanger defined in claim 17, further comprising an additional cooling coil disposed between said outer tube bundle and the wall of said vessel, and connected in parallel with the outer tube bundle, the manifold pipe of the outer tube bundle being connected via a closable bypass line with manifold pipe of the inner tube bundle whereby the additional cooling coil and the feed to the outer tube bundle can be closed off independently from one another.

26. The heat exchanger defined in claim 17, further comprising a support plate extending across said vessel between the bottom and said end of said partition, said support plate being provided with gas-permeable openings.

27. The heat exchanger defined in claim 17, further comprising filters along said ducts for removing contaminants from said second fluid.

28. The heat exchanger defined in claim 17 wherein each of said tube bundles comprises a multiplicity of layers of helically coiled tubes each of said layers having a plurality of such tubes.

* * * * *